US00PP16562P3

(12) United States Plant Patent
Dofferhoff

(10) Patent No.: US PP16,562 P3
(45) Date of Patent: May 23, 2006

(54) ***GENTIANA* PLANT NAMED 'MARSHA'**

(50) Latin Name: *Gentiana makinoi*
Varietal Denomination: Marsha

(76) Inventor: Hans Dofferhoff, Middelburgseweg 1, Reeuwijk (NL), 2811 PL ( * ) Notice: Subject to any disclaimer, the term of this patent is extended or adjusted under 35 U.S.C. 154(b) by 313 days.

(21) Appl. No.: 10/950,871

(22) Filed: Sep. 27, 2004

(65) Prior Publication Data

US 2006/0070152 P1 Mar. 30, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Penny J. Aguirre

(57) ABSTRACT

A new cultivar of Gentian, *Gentiana makinoi* 'Marsha', characterized by its large, deep blue flowers borne on thick, strong stems combined with a plant habit that is compact, short and uniform in height.

2 Drawing Sheets

Botanical classification: *Gentiana makinoi.*
Varietal denomination: 'Marsha'.

BACKGROUND OF THE INVENTION

The present invention relates to a new and distinct cultivar of *Gentiana makinoi* and will be referred to hereafter by its cultivar name, 'Marsha'. 'Marsha' represents a new Gentian, an herbaceous perennial grown for landscape use.

The inventor discovered the new cultivar, 'Marsha', as a chance seedling that arose in a cultivated area in his nursery in Reeuwijk, The Netherlands in the summer of 1996. Although the parentage is unknown, the characteristics of the new cultivar and the presence of the cultivar *Gentiana makinoi* 'Royal Blue' (not patented) in the nursery suggest that 'Royal Blue' is a likely parent.

The new cultivar 'Marsha' was selected for its unique characteristics in plant habit combined with the deep blue flowers that are characteristic of 'Royal Blue'. In comparison to 'Royal Blue', 'Marsha' has thicker stems, a more compact growth habit, and a plant height that is shorter and more uniform.

Asexual reproduction of the new cultivar was first accomplished by taking stem cuttings in Reeuwijk, The Netherlands in 1996. 'Marsha' was subsequently propagated by tissue culture. It has been determined by propagation both by stem cuttings and tissue culture that the characteristics of the new cultivar are stable and are reproduced true to type in successive generations.

SUMMARY OF THE INVENTION

The following traits have been repeatedly observed and represent the characteristics of the new cultivar after observing plants grown outdoors in a field for two years in Reeuwijk, The Netherlands. These attributes in combination distinguish 'Marsha' from 'Royal Blue' and all other varieties of Gentians known to the inventor.

1. Large, deep blue colored flowers.
2. Compact growth habit, reaching about 40 cm in height and 50 cm in spread.

3. Flowers are borne on thicker, strong stems in comparison to 'Royal Blue'.
4. Stems are more uniform in height in comparison to 'Royal Blue'.
5. Shorter in height than 'Royal Blue'.
6. Suitable as a cut flower.

BRIEF DESCRIPTION OF THE PHOTOGRAPHS

The plants and plant parts in the photographs depict a two-year old plant of 'Marsha' as grown outdoors in a field plot in Reeuwijk, The Netherlands.

The photograph on the first sheet provides an overall view of the new Gentian in bloom.

The photograph on the top of the second sheet is a close-up view of the flowers of 'Marsha' and the photograph on the bottom of the second sheet is a close-up view of a leaf of 'Marsha'.

The colors in the photographs are as close as possible with the photographic and printing technology utilized. The color values cited in the detailed botanical description accurately describe the colors of the new Gentian.

DETAILED BOTANICAL DESCRIPTION

The following is a detailed description of the new cultivar as grown outdoors in fertile, well drained soil in full sun in The Netherlands for 2 years with average day temperatures ranging from 17° C. to 32° C. and average night temperatures ranging from 10° C. to 19° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Sociey, London, England, except where general color terms of ordinary dictionary significance are used.

Botanical classification: 'Marsha' is a cultivar of *Gentiana makinoi.*

Parentage: Naturally occurring chance seedling of *Gentiana makinoi*, parentage is unknown, *Gentiana makinoi* 'Royal Blue' is a likely parent.

General description:

*Blooming period.*—Continuously from mid July to early September in The Netherlands.

*Plant type.*—Herbaceous perennial.

*Plant habit.*—Clump-forming, upright, compact, triangular in overall shape.

*Growth rate.*—Moderate growth rate.

*Height and spread.*—Average of 40 cm in height, 50 cm in spread.

*Hardiness.*—USDA Zone 6 to 8.

*Culture.*—Prefers humus-rich, moist but well-drained soils in partial shade or full sun in areas where summers are cool with sufficient moisture.

*Diseases and pests.*—No unique susceptibility or resistance to disease or pests known to affect *Gentiana makinoi* has been observed for 'Marsha'.

*Root description.*—Fine.

Growth and propagation:

*Propagation.*—Stem cuttings and tissue culture.

*Root initiation.*—Roots appear on cuttings in about 10 days when grown at about 25° C. in a greenhouse without supplemental lighting during the summer months.

*Root development.*—Roots fully develop in a 13 cm pots in about 3 months from a rooted cutting.

*Cropping time to bloom.*—Approximately 10 months when field grown.

Stem description:

*Stem shape.*—Round.

*Stem color.*—144A (yellow-green) tinted with 177B to 177C (greyed-orange) on upper one half of stem.

*Stem size.*—Up to about 43 cm in length, up to about 5 cm in diameter.

*Stem surface.*—Slightly glossy.

*Stem aspect.*—Held strongly erect.

*Internode length.*—Average of 2.4 cm.

*Branching habit.*—All shoots arise from base, no secondary branching, 2 year-old plant produces an average of 7 stems.

Foliage description:

*Leaf shape.*—Narrowly elliptic.

*Leaf division.*—Simple.

*Leaf base.*—Cuneate.

*Leaf apex.*—Acute.

*Leaf venation.*—Tri-nerved, leave aspect is concave in respect to the mid rib on the upper surface, mid rib is conspicuous, veins are 144B in color on the upper and lower surface.

*Leaf margins.*—Entire.

*Leaf attachment.*—Sessile.

*Leaf arrangement.*—Opposite.

*Leaf surface.*—Upper and lower surface; glabrous, slightly leathery, upper leaves become glaucous when mature.

*Leaf color.*—Immature: upper; 137A to 141A, lower; 138A to 138B. Mature: upper; 137A to 139A, lower; 138A.

*Leaf number.*—Average of 36 per stem (18 pairs).

*Leaf size.*—Average of 9 cm in length and 2.3 cm in width.

Flower description:

*Flower type.*—Axillary and terminal tubular flowers, arising singularly or in clusters.

*Flower fragrance.*—None.

*Flower lastingness.*—Average of 10 days on plant, average of 14 days as a cut flower, persistent.

*Rate of flower opening.*—Approximately 25% is opened at any stage, approximately 50% are open at peak of flowering period.

*Flower bud description.*—Oblong in shape, average of 8 mm in diameter and 2.9 cm in length, petal portion is 96C to 96D in color and calyx portion is 145B in color.

*Flower quantity.*—Average of 26 per stem, approximately 180 per 7 stem plant.

*Flower aspect.*—Held upright.

*Flower shape.*—Tubular with 25% of flower opening.

*Flower size.*—4.5 cm in depth, 1.8 cm in diameter.

*Peduncle description.*—Present on lateral flowers, not present on terminal flowers, about 3.9 cm in length and 2 mm in width, held at an angle of about 10° relative to stem, 144A to 144B in color.

*Petal description.*—5, oblong in shape, 75% of lower portion is fused into a tubular shape, margin is entire, apex is acute, surface is smooth and slightly glossy in appearance.

*Petal size.*—About 4.5 cm in length and 9 mm in width.

*Petal color.*—Outer surface 96A striped with 96B to 96C (opening and fully open), inner surface 96C striped with 97D (opening and fully open), petals fade to 96A to 99A on lower half and 86B on upper half (both surfaces).

*Calyx form.*—Campanulate.

*Calyx size.*—Average of 2.4 cm in length and 1.4 cm in diameter.

*Sepal description.*—6 (average), linear in shape, margin is entire, apex is acute, base is cuneate and fused, surface is smooth and dull in appearance.

*Sepal size.*—Average of 2.4 cm in length, 4 mm in width.

*Sepal color.*—Lower surface; 145B (opening and mature), upper surface; 141A to 141B when opening and 138B when mature.

Reproductive organs:

*Gynoecium.*—1 Pistil about 2.8 cm in length, stigma is decurrent and 149D in color, style is about 2.6 cm in length and 145A to 145B in color with a lighter base of 145D, ovary is 145A in color.

*Androcoecium.*—5 stamens, anthers are oblong in shape, basifixed, about 4 mm in length, 0.5 mm in width and 4A to 4B in color, filaments are about 2.3 mm in length and 155C in color, pollen is moderately abundant and 3A to 4A in color.

*Fruit.*—No fruit has been observed under the conditions tested.

It is claimed:

1. A new and distinct cultivar of *Gentiana* plant named 'Marsha' as herein illustrated and described.

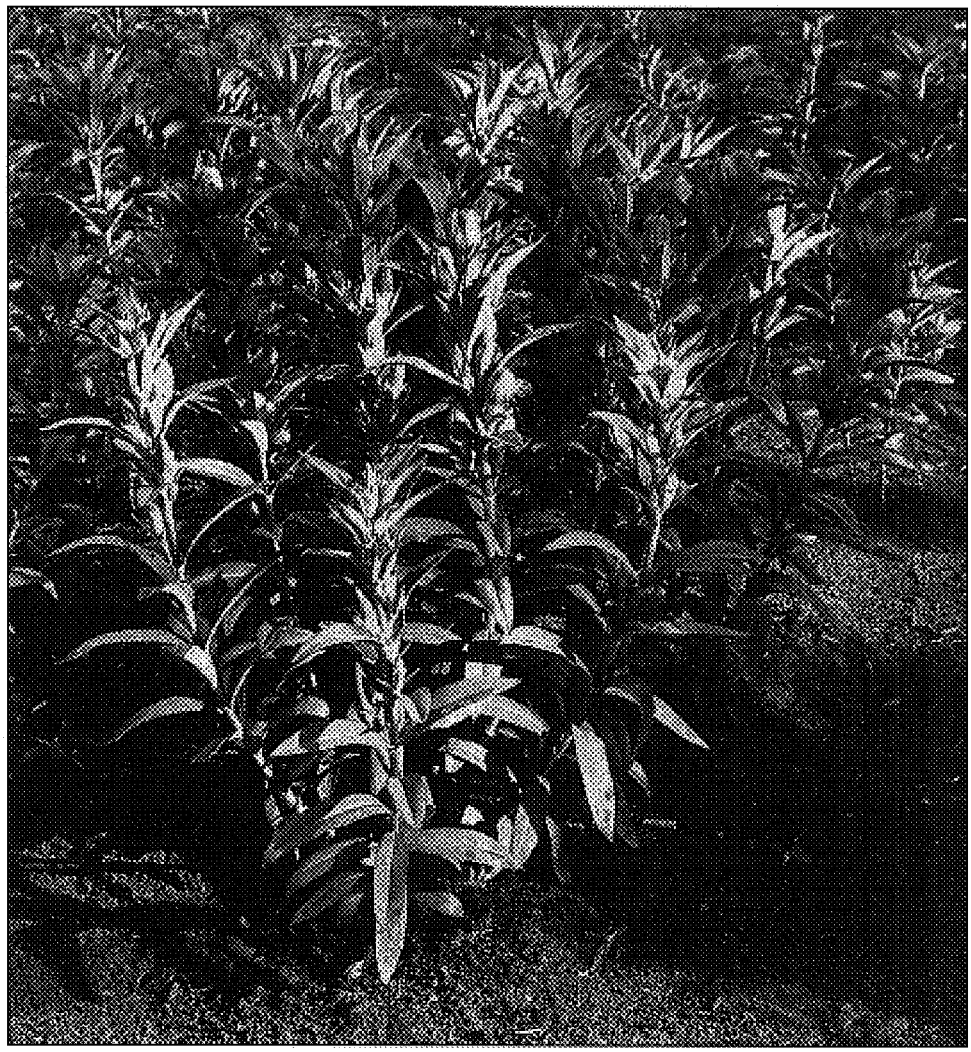

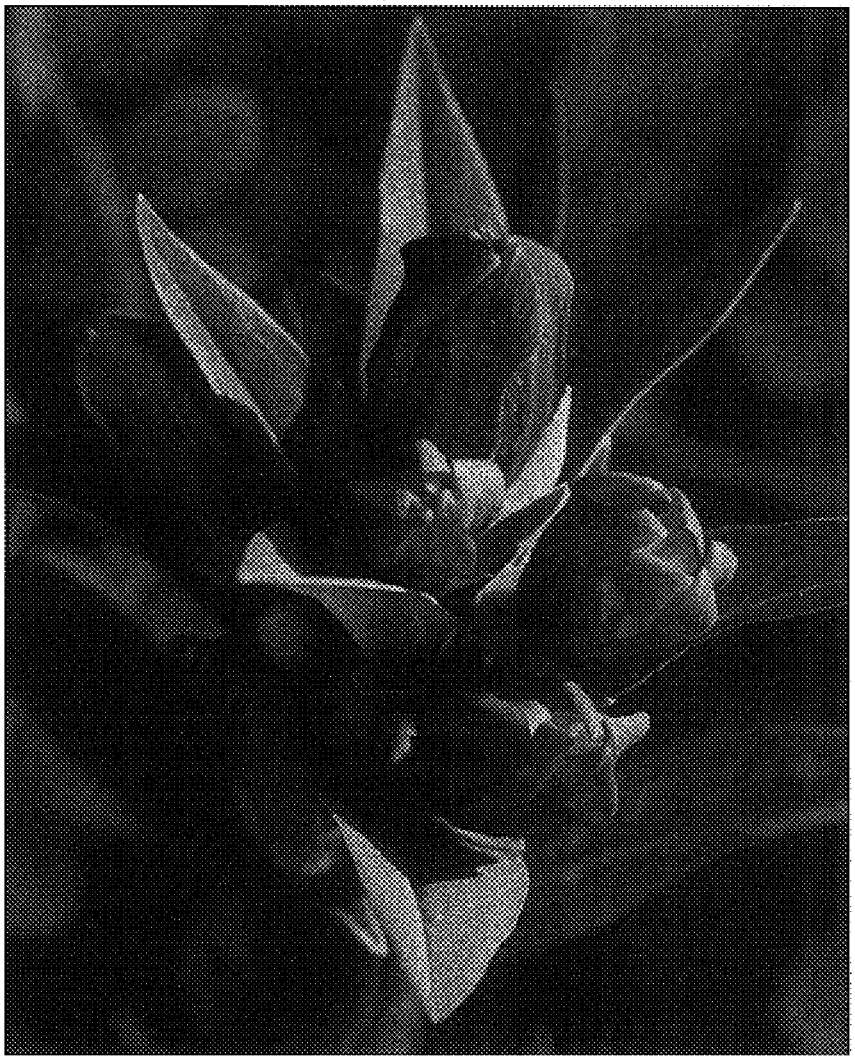
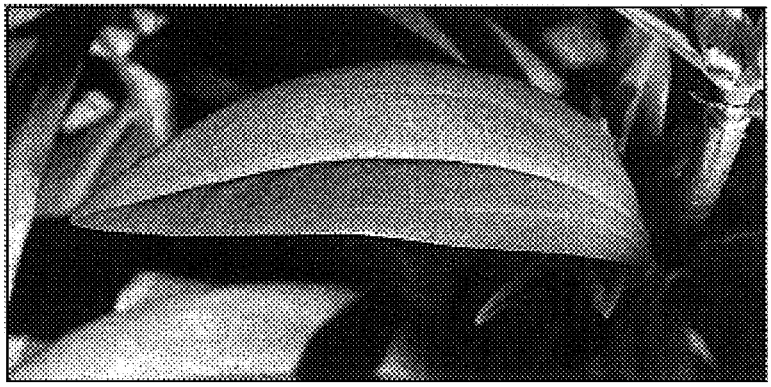

* * * * *